United States Patent
Dacosta et al.

(10) Patent No.: US 11,433,014 B2
(45) Date of Patent: *Sep. 6, 2022

(54) POLYOL POLYRHAMNOSIDES, PROCESS FOR THE PREPARATION THEREOF, AND COSMETIC AND/OR PHARMACEUTICAL COMPOSITION COMPRISING SAME

(71) Applicant: SOCIETE D'EXPLOITATION DE PRODUITS POUR LES INDUSTRIES CHIMIQUES SEPPIC, Paris (FR)

(72) Inventors: Georges Manuel Dacosta, Saix (FR); Jérome Guilbot, Castres (FR); Stéphane Dessilla, Castres (FR); Laetitia Cattuzzato, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 168 days.

This patent is subject to a terminal disclaimer.

(21) Appl. No.: 16/772,364

(22) PCT Filed: Nov. 27, 2018

(86) PCT No.: PCT/FR2018/053009
§ 371 (c)(1),
(2) Date: Jun. 12, 2020

(87) PCT Pub. No.: WO2019/115903
PCT Pub. Date: Jun. 20, 2019

(65) Prior Publication Data
US 2021/0386647 A1    Dec. 16, 2021

(30) Foreign Application Priority Data
Dec. 12, 2017 (FR) .................................. 1761983

(51) Int. Cl.
*A61K 8/73* (2006.01)
*A61K 8/34* (2006.01)
*A61K 8/60* (2006.01)
*A61Q 1/14* (2006.01)
*A61Q 5/02* (2006.01)
*A61Q 19/00* (2006.01)

(52) U.S. Cl.
CPC ................ *A61K 8/73* (2013.01); *A61K 8/345* (2013.01); *A61K 8/60* (2013.01); *A61Q 1/14* (2013.01); *A61Q 5/02* (2013.01); *A61Q 19/007* (2013.01)

(58) Field of Classification Search
None
See application file for complete search history.

(56) References Cited

U.S. PATENT DOCUMENTS

| | | | |
|---|---|---|---|
| 5,891,854 | A | 4/1999 | Thiem et al. |
| 6,305,647 | B1 | 10/2001 | Defendini et al. |
| 8,088,742 | B2 | 1/2012 | Stoltz et al. |
| 8,288,353 | B2 | 10/2012 | Stoltz et al. |
| 2006/0088491 | A1 | 4/2006 | Stoltz et al. |
| 2011/0144316 | A1 | 6/2011 | Stoltz et al. |

FOREIGN PATENT DOCUMENTS

| | | |
|---|---|---|
| DE | 102011081436 | 6/2012 |
| EP | 0 770 378 | 5/1997 |
| FR | 2 839447 | 11/2003 |
| FR | 2876283 | 4/2006 |
| FR | 3050935 | 11/2017 |
| JP | S63-063390 A | 3/1988 |
| JP | 2014-058472 | 4/2014 |

OTHER PUBLICATIONS

International Search Report, PCT/FR2018/053009, dated Apr. 1, 2019.
French Search Report, FR 1761983, dated Aug. 21, 2018.

*Primary Examiner* — Nicole P Babson
(74) *Attorney, Agent, or Firm* — Nixon & Vanderhye

(57) ABSTRACT

Disclosed is a composition based on a polyol of formula: $HO-CH_2-(CHOH)_m-CH_2-OH$ and on alkyl polyrhamnosides of formula: $HO-CH_2-(CHOH)_m-CH_2-O-(Rham)_x-H$; process for preparing same, and cosmetic or pharmaceutical composition including same.

20 Claims, No Drawings

POLYOL POLYRHAMNOSIDES, PROCESS FOR THE PREPARATION THEREOF, AND COSMETIC AND/OR PHARMACEUTICAL COMPOSITION COMPRISING SAME

BACKGROUND OF THE INVENTION

Field of the Invention

The present invention relates to a novel composition based on sugar derivatives, to the process for preparing same and to the use thereof in cosmetic and pharmaceutical compositions.

The invention mainly finds application in cosmetics and pharmaceuticals.

Description of the Related Art

The skin is an atypical organ of the human body, which is extremely thin with regard to its extent, but also an individual's heaviest organ. One of the characteristics of the skin lies in the fact that it is an interface organ, a boundary organ, between the internal medium (human body) and the external medium. As a result, and with the flora which covers it and lives thereon, the skin is the first barrier for protecting the human body. On account of its interface position with the external medium, the skin is subjected to numerous daily stresses, for instance contact with clothing, temperature changes, changes in degrees of hygrometry, pressure changes, or even attack, for instance contact with certain chemical products which have or potentially have a very acidic, very basic or irritant nature, and with chemical products considered as pollutants. The skin is composed of layers of different tissues:

the epidermis, composed of keratinocytes, is its outermost part, followed by
the dermis, which is a connective tissue mainly composed of fibroblasts and of extracellular matrix, and
the hypodermis, consisting of adipocytes, which is the deepest part and the part that is the most remote from the external medium.

The skin performs its various functions in the interest of the entire system that it shelters, among which the following may be recalled:

a mechanical barrier function to ensure the integrity of the internal medium of the body,
an emunctorial function directed toward secreting sweat based on water, salts and acidic waste,
a function of regulating the body temperature, and contains many other regulatory mechanisms, for instance its mechanism for adapting to and protecting against ultraviolet radiation (adaptive pigmentary coloring by producing melanin), for instance an immune monitoring system via the presence of macrophages and dendritic cells.

Human skin also constitutes the first image seen by others. Consequently, improving its appearance is a subject of constant concern for humans. The skin is the reflection of a state of well-being, often associated with youthfulness, and, conversely, with a state of fatigue and/or aging. As a result, preserving and improving the state of the outermost layer of the skin, namely the epidermis, is a major focus for the research conducted by the cosmetics industries.

At the periphery of the epidermis is an upper cornified layer known as the *Stratum corneum*, which is the first layer of the epidermis to suffer the stresses of external origin, such as variations in external climatic conditions (temperature, pressure, hygrometry) or mechanical stresses. This is why improving the appearance or maintaining the satisfactory appearance of human skin consists notably in maintaining a state of moisturization of the *Stratum corneum* at an optimum and satisfactory level. This also makes it possible to avoid esthetic and physiological drawbacks associated with dryness of the skin.

The *Stratum corneum* has a tendency to become dehydrated and to dry out when it is exposed to low humidity or when it is placed in prolonged and frequent contact with a detergent solution.

Many solutions have already been provided to solve the problems of skin dryness caused by dehydration of the *Stratum corneum*, notably by developing moisturizing compositions.

However, to prevent the skin from degrading too quickly, it is necessary to provide short-term skin moisturization, which acts within a short time, notably in the case of exposure of the hands, the lips and the face to climatic conditions (intense cold, wind) which induce rapid drying-out of the skin.

To evaluate and assess the healthiness of the skin and its correct functional state, and more particularly its moisturization, two measurements are commonly used, for their reliability and their robustness:

Measurement of the degree of moisturization in the *Stratum corneum*, i.e. the water content therein, and measurement of the transepidermal water loss (or TWL), i.e. the flow of water that evaporates from the skin via the *Stratum corneum*, due to the passive diffusion of water from the deepest layers of the skin to the external medium and due to perspiration, which can be detected at any moment at its surface.

The degree of moisturization of the skin is measured via biometrological techniques notably based on skin capacitance or skin impedance measurements. Various commercial machines are available for performing such measurements. An increase in the impedance or in the capacitance indicates an increase in the degree of moisturization of the skin and consequently in the water content of the *Stratum corneum*.

The transepidermal water loss (TWL) is measured via biometrological techniques consisting in applying, to the surface of the skin and under standardized conditions, an instrument consisting of an open cylinder in which a probe measures, dynamically, the water evaporation flow. As a complement to this conventional open cylinder technique, similar instruments based on a closed cylinder (closed chamber) have more recently been developed and are also available. A decrease in the "transepidermal water loss" measured at the surface of the *Stratum corneum* indicates a reduction in the evaporation of the contained water.

With regard to these preceding definitions, an improvement in the moisturization of the skin, and more particularly of the *Stratum corneum*, may be imagined by placing the skin in contact with compounds which have a "moisturizing effect".

A challenge of skin moisturization, and thus of the research related thereto, is that of developing substances or compositions which are characterized by an improved moisturizing effect without, however, needing to induce a substantial occlusive effect, said occlusive effect possibly causing disruptions in the natural functioning of "non-pathological" skin, namely skin which does not have a transepidermal water loss of greater than $10 \text{ g/m}^2/\text{h}$, and thus proving to be contrary to the desired aim.

The following are moisturizers for the skin, and more particularly for very dry and destructured skin:

occlusive agents, which are characterized by their ability to form an impermeable film on the surface of the skin and thus to greatly reduce the evaporation of water at the surface of the epidermis. Examples of such agents include mineral oils, for instance petroleum jelly or liquid paraffins, glycerol, shea butter (*Butyrospermum parkii* butter), beeswax, certain plant oils such as wheat germ oil, coconut oil, cocoa butter, lanolin and silicone derivatives;

emollients, which are characterized by their ability to fill the intercellular spaces existing between corneocytes (cells of the cornified layer of the epidermis); they also limit the evaporation of water from the epidermis, but to a lesser extent than occlusive agents. Examples of such agents include ceramides, linoleic acid and certain plant oils such as sweet almond oil or jojoba oil;

film-forming agents, which are characterized by their ability to associate with water to form semipermeable hydrogels; they thus participate in modulating the evaporation of water from the *Stratum corneum*. Examples of such agents include collagen, elastin, DNA, pectin, gelatin, chitosan, or glycosaminoglycans such as hyaluronic acid;

humectants, which are hydrophilic substances characterized by their high hygroscopic power, i.e. their ability to retain water. They thus contribute toward enabling the *Stratum corneum* to conserve both the water it contains and the water provided by the cosmetic formula. Examples of such agents include urea, glycerol, lactic acid, amino acids, sodium lactate, propylene glycol, polyethylene glycols, α-hydroxy acids or sorbitol. Glycerol, urea and lactic acid are the humectants most frequently used in moisturizing cosmetic compositions, most particularly glycerol for its very competitive price.

However, certain humectants such as glycerol also have an immediate occlusive effect, which is not desired for normal skin whose barrier function is not deficient. Furthermore, some of them, such as glycerol, cause certain skin and mucous membrane irritations in the case of particularly sensitive people.

The search for novel moisturizing substances that are better tolerated than glycerol has notably led to the use of certain derivatives thereof, in particular glycerol acetals, resulting from its condensation with a reducing sugar. Mention may notably be made of:

acetals obtained from the condensation of glycerol with glucose, which are disclosed in the European patent application published under the number EP 0 770 378; they effectively have better skin tolerance than glycerol, but have generally lower moisturizing power;

mannosyl erythritol described in the Japanese patent application published under the number JP 63063390 A2, which is obtained according to an enzymatic preparation process, and which is known for its activity in skin moisturization retention.

Among the acetals of glucose and of other polyols, mention may be made of glycosides obtained by acetalization of erythritol, xylitol or sorbitol, as described in the French patent application published under the number FR 2 839 447 A1. These compounds have demonstrated better moisturizing properties than the abovementioned glycerol acetalization products.

Polyol polyglycosides (or PPG) are obtained in the same manner as alkylpolyglucosides (or APG) from glucose, by replacing the starting fatty alcohols with polyols. At the end of the glycosylation reactions, the products may be sold as obtained in solution in the starting polyol or in the form of aqueous solutions. In a similar manner to APGs, the target PPGs are characterized by an average degree of polymerization (DP) very close to 1. Only polyol polyglucosides are commercially available, namely glycerol polyglucoside under the brand name Hydragen™ GG and a composition comprising xylityl polyglucoside under the brand name Aquaxyl™.

SUMMARY OF THE INVENTION

In the context of their research with regard to improving skin moisturization, the inventors focused on developing a novel technical solution based on the use of a natural sugar never used in this context, rhamnose, the natural source of which is wood hemicellulose, notably that from birch or from beech:

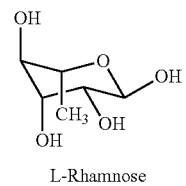

L-Rhamnose

Thus, according to a first aspect, a subject of the invention is a composition ($C_1$) comprising, per 100% of its mass:

(1)—an amount of greater than 0% by mass and less than or equal to 25% by mass of a polyol of formula (I):

$$HO—CH_2—(CHOH)_m—CH_2—OH \qquad (I);$$

in which formula (I) m represents an integer equal to 2, 3 or 4;

(2)—an amount of greater than 0% by mass and less than or equal to 30% by mass of one or more anhydrides of said polyol of formula (I);

(3)—from 60% by mass to 95% by mass of a composition ($C_R$) represented by formula (II):

$$HO—CH_2—(CHOH)_m—CH_2—O-(Rham)_x-H \qquad (II),$$

in which formula (II) Rham represents the rhamnose residue, m is as defined previously in formula (I) and x, which indicates the average degree of polymerization of said Rham residue, represents a decimal number greater than 1.0 and less than or equal to 2.5, (4)—an amount of greater than 0% by mass and less than or equal to 5% by mass of rhamnose.

The term "polyol anhydride of formula (I)" notably denotes, when m represents the number 2, the compound of formula ($B_{11}$), when m represents the number 3, the compound of formula ($B_{12}$) and when m represents the number 4, the compounds of formulae ($B_{13}$) and ($B_{14}$):

(B11)

(B12)

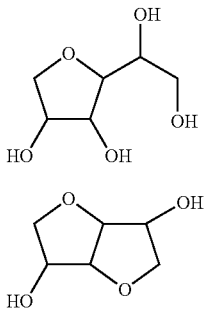

(B13)

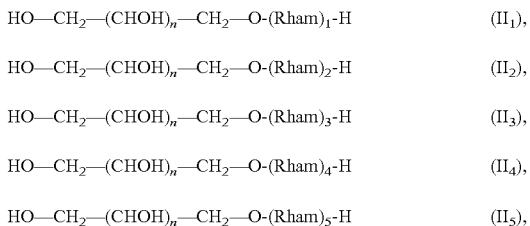

(B14)

The term "formula (II) $HO-CH_2-(CHOH)_n-CH_2-O-(Rham)_x-H$" means that said composition ($C_R$) consists essentially of a mixture of compounds represented by formulae $(II_1)$, $(II_2)$, $(II_3)$, $(II_4)$ and $(II_5)$:

$HO-CH_2-(CHOH)_n-CH_2-O-(Rham)_1-H$    $(II_1)$, $HO-CH_2-(CHOH)_n-CH_2-O-(Rham)_2-H$    $(II_2)$, $HO-CH_2-(CHOH)_n-CH_2-O-(Rham)_3-H$    $(II_3)$, $HO-CH_2-(CHOH)_n-CH_2-O-(Rham)_4-H$    $(II_4)$, $HO-CH_2-(CHOH)_n-CH_2-O-(Rham)_5-H$    $(II_5)$, in the respective molar proportions $a_1$, $a_2$, $a_3$, $a_4$ and $a_5$, such that the sum $a_1+a_2+a_3+a_4+a_5$ is equal to 1 and such that the sum $a_1+2a_2+3a_3+4a_4+5a_5$ is equal to x.

In the preceding definition, the term "essentially" indicates that the presence of one or more compounds of formula $(II_w)$ with w greater than 5 is not excluded in composition ($C_R$), but that if it is present, then it is present in minimal proportions which do not entail any substantial modification of the properties of said composition ($C_R$).

In formula (II) as defined above, the group $HO-CH_2-(CHOH)_n-CH_2-O-$ is linked to $(Rham)_x$ via the anomeric carbon of the saccharide residue, so as to form an acetal function.

According to a particular aspect of the present invention, x represents in formula (II) a decimal number greater than or equal to 1.2 and less than or equal to 2.2.

According to another particular aspect, a subject of the invention is composition ($C_1$) as defined previously, for which, in formulae (I) and (II), m represents the number 2.

According to another particular aspect, a subject of the invention is composition ($C_1$) as defined previously, for which, in formulae (I) and (II), m represents the number 3; and more particularly composition $C_1$ as defined previously, comprising, per 100% of its mass:

(1)—up to 25% by mass of the compound of formula:

$HO-CH_2-(CHOH)_3-CH_2-OH$ (2)—up to 5% by mass of the compound of formula ($B_{12}$) as defined previously;

(3)—from 70% by mass to 95% by mass of a composition ($C_{R3}$) represented by the formula:

$HO-CH_2-(CHOH)_3-CH_2-O-(Rham)_x-H$;

(4)—up to 2% by mass of rhamnose.

According to another particular aspect, a subject of the invention is composition ($C_1$) as defined previously, for which, in formulae (I) and (II), m represents the number 4; and more particularly composition $C_1$ as defined previously, comprising, per 100% of its mass:

(1)—up to 25% by mass of the compound of formula:

$HO-CH_2-(CHOH)_4-CH_2-OH$;

(2)—up to 30% by mass of the compound of formula ($B_{13}$) as defined previously, alone or in combination with the compound of formula ($B_{14}$) as defined previously;

(3)—from 70% by mass to 95% by mass of a composition ($C_{R4}$) represented by the formula:

$HO-CH_2-(CHOH)_4-CH_2-O-(Rham)_x-H$;

(4)—up to 4% by mass of rhamnose.

According to another particular aspect, composition ($C_1$) as defined previously comprises, per 100% of its mass:

(1)—up to 25% by mass of the compound of formula:

$HO-CH_2-(CHOH)_4-CH_2-OH$;

(2)—up to 25% by mass of the compound of formula ($B_{13}$) as defined previously;

(2')—up to 5% by mass of the compound of formula ($B_{14}$) as defined previously;

(3)—from 70% by mass to 95% by mass of said composition ($C_{R4}$):

$HO-CH_2-(CHOH)_4-CH_2-O-(Rham)_x-H$; and (4)—up to 2% by mass of rhamnose.

Composition ($C_1$) as defined previously may optionally comprise water, mainly in a proportion of less than or equal to 5% of its mass.

A subject of the invention is also a process for preparing composition ($C_1$) as defined previously, characterized in that it comprises the following successive steps:

a step a) of heating, with gentle stirring, the polyol of formula (I) as defined previously, until it is brought to a higher temperature ($T_1$) of at least 5° C. above its melting point;

a step b) of dispersing, with stirring, rhamnose monohydrate in the previously molten medium in the desired stoichiometric ratio;

a step c) of acetalization by adding, with stirring, to the liquid medium obtained from step b), a catalytic amount of strong acid, while maintaining all the reaction mixture under partial vacuum and distilling off the water formed; and, if necessary or if desired, a step d) of neutralizing the solution obtained on conclusion of step d), to obtain said composition ($C_1$).

When the polyol of formula (I) is xylitol or sorbitol, the temperature ($T_1$) is greater than or equal to 95° C. and less than or equal to 135° C. and more particularly greater than or equal to 105° C. and less than or equal to 135° C.

When the polyol of formula (I) is erythritol, the temperature ($T_1$) is greater than or equal to 120° C. and less than or equal to 135° C. and more particularly less than or equal to 130° C.

According to a first alternative of the process as defined previously, in the implementation of step a), the sorbitan of formula (B13) is used instead of sorbitol.

For the implementation of step c) as defined above, the strong acid is notably chosen from sulfuric acid, hydrochloric acid, phosphoric acid, nitric acid, hypophosphorous acid, methanesulfonic acid, para-toluenesulfonic acid, trifluoromethanesulfonic acid and acidic ion-exchange resins. Usually, the acetalization reaction is performed at a temperature ($T_2$) from 70° C. to 130° C., under a vacuum of from 300 to $20 \times 10^2$ Pa (300 to 20 mbar).

Composition ($C_1$) as defined previously may be incorporated into any type of cosmetic or pharmaceutical composition intended to be applied to the skin or mucous membranes.

This is why a subject of the invention is also a topical cosmetic or dermocosmetic composition (C'), characterized in that it comprises an effective amount of composition ($C_1$) as defined previously.

A subject of the invention is also a topical pharmaceutical or dermopharmaceutical composition (C'), characterized in that it comprises an effective amount of composition ($C_1$) as defined previously.

In the abovementioned definitions of compositions (C) and (C'), the term "effective amount" denotes a mass proportion generally greater than or equal to 0.5% by mass and less than or equal to 5%, of their total mass and more particularly from 1% by mass to 3% by mass of their total mass.

The adjective "topical" qualifying the abovementioned compositions (C) and (C') means that these compositions are used by application to the skin, the scalp or mucous membranes.

Said abovementioned compositions (C) and (C') are notably in the form of an aqueous or oily solution, an emulsion or a microemulsion of the water-in-oil (W/O) or oil-in-water (O/W) type, a multiple emulsion of water-in-oil-in-water (W/O/W) or oil-in-water-in-oil (O/W/O) type, a gel, a soap or a syndet, a balm, an aqueous dispersion, a cream, a mousse or an aerosol, or alternatively in anhydrous form such as a powder. They may be used as cream, milk, bubble bath, shampoo, hair conditioner or lotion for caring for or protecting the face, the hands and the body, more particularly for their short-term moisturizing effect on the epidermis after prolonged exposure to low temperatures, or to solar radiation; or alternatively for preventing or slowing down the appearance of the external signs of aging of human skin, for instance the appearance of wrinkles, fine lines, impairment of the microrelief, lack of elasticity and/or tonicity, lack of density and/or firmness of human skin; or alternatively after shaving the face or for washing and/or treating the scalp.

In general, said compositions (C) and (C') also include excipients and/or active principles usually used in the field of topical formulations, for instance foaming and/or detergent surfactants, thickening and/or gelling surfactants, thickeners and/or gelling agents, stabilizers, film-forming compounds, solvents and cosolvents, hydrotropic agents, plasticizers, fatty substances, oils and waxes, emulsifiers and coemulsifiers, opacifiers, nacreous agents, overfatting agents, sequestrants, chelating agents, antioxidants, fragrances, essential oils, preserving agents, conditioning agents, bleaching agents intended for bleaching bodily hair and the skin, active principles intended to provide a treating and/or protective action to the skin or the hair, sunscreens, mineral fillers or pigments, particles that give a visual effect or that are intended for encapsulating active agents, exfoliant particles, texture agents, optical brighteners and insect repellents.

As examples of foaming and/or detergent surfactants optionally present in said compositions (C) and (C') as defined previously, mention may be made of the topically acceptable anionic, cationic, amphoteric or nonionic foaming and/or detergent surfactants commonly used in this field of activity.

Among the foaming and/or detergent anionic surfactants optionally present in said compositions (C) and (C') as defined previously, mention may be made of alkali metal salts, alkaline-earth metal salts, ammonium salts, amine salts and amino alcohol salts, of alkyl ether sulfates, of alkyl sulfates, of alkylamido ether sulfates, of alkylaryl polyether sulfates, of monoglyceride sulfates, of α-olefin sulfonates, of paraffin sulfonates, of alkyl phosphates, of alkyl ether phosphates, of alkylsulfonates, of alkylamide sulfonates, of alkylarylsulfonates, of alkylcarboxylates, of alkylsulfosuccinates, of alkyl ether sulfosuccinates, of alkylamide sulfosuccinates, of alkylsulfoacetates, of alkylsarcosinates, of acylisethionates, of N-acyltaurates, of acyllactylates, of N-acyl derivatives of amino acids, of N-acyl derivatives of peptides, of N-acyl derivatives of proteins, of fatty acids.

Among the foaming and/or detergent amphoteric surfactants optionally present in said compositions (C) and (C') as defined previously, there are alkylbetaines, alkylamidobetaines, sultaines, alkylamidoalkylsulfobetaines, imidazoline derivatives, phosphobetaines, amphopolyacetates and amphopropionates.

Among the foaming and/or detergent cationic surfactants optionally present in said compositions (C) and (C') as defined previously, there are in particular quaternary ammonium derivatives.

Among the foaming and/or detergent nonionic surfactants optionally present in said compositions (C) and (C') as defined previously, there are more particularly alkylpolyglycosides, castor oil derivatives, polysorbates, coconut kernel amides and N-alkylamines.

Among the foaming and/or detergent nonionic surfactants optionally present in said compositions (C) and (C') as defined previously, there is more particularly composition ($O_3$) or a mixture of compositions ($O_3$), said composition ($O_3$) being represented by formula (IV):

$$R_2-O-(G_2)_p-H \quad \text{(IV)}$$

in which $R_2$ represents a linear or branched, saturated or unsaturated aliphatic radical including from 8 to 16 carbon atoms, $G_2$ represents a reducing sugar residue and p represents a decimal number greater than or equal to 1.05 and less than or equal to 5, said composition ($O_3$) consisting essentially of a mixture of compounds represented by formulae ($IV_1$), ($IV_2$), ($IV_3$), ($IV_4$) and ($IV_5$):

$$R_2-O-(G_2)_1-H \quad (IV_1),$$

$$R_2-O-(G_2)_2-H \quad (IV_2),$$

$$R_2-O-(G_2)_3-H \quad (IV_3),$$

$$R_2-O-(G_2)_4-H \quad (IV_4),$$

$$R_2-O-(G_2)_5-H \quad (IV_5),$$

in the respective molar proportions $a_1$, $a_2$, $a_3$, $a_4$ and $a_5$, such that the sum $a_1+a_2+a_3+a_4+a_5$ is equal to 1 and such that the sum $a_1+2a_2+3a_3+4a_4+5a_5$ is equal to p.

As examples of thickening and/or gelling surfactants optionally present in said compositions (C) and (C') as defined previously, mention may be made of optionally alkoxylated alkylpolyglycoside fatty esters, and most particularly ethoxylated methylpolyglucoside esters, such as the PEG 120 methyl glucose trioleate or the PEG 120 methyl glucose dioleate sold, respectively, under the names Glutamate™ LT and Glutamate™ DOE120; alkoxylated fatty esters, such as the PEG 150 pentaerythrityl tetrastearate sold under the name Crothix™ DS53, the PEG 55 propylene glycol oleate sold under the name Antil™ 141; fatty-chain polyalkylene glycol carbamates, for instance the PPG14 laureth isophoryl dicarbamate sold under the name Elfacos™ T211, the PPG14 palmeth 60 hexyl dicarbamate sold under the name Elfacos™ GT2125.

As examples of emulsifying surfactants optionally present in said compositions (C) and (C') as defined previously, mention may be made of nonionic surfactants, anionic surfactants and cationic surfactants.

As examples of emulsifying nonionic surfactants optionally present in said compositions (C) and (C') as defined previously, mention may be made of fatty acid esters of sorbitol, for example Montane™ 80, Montane™ 85 and Montane™ 60; linear or branched, saturated or unsaturated alkylpolyglycosides and compositions of alkylpolyglycosides and of fatty alcohols, the alkyl chains of said alkyl polyglycosides consisting of linear or branched, saturated or unsaturated alkyl groups including from 14 to 22 carbon atoms, for example Montanov™ Easynov™ and Fluidanov™; fatty acid esters of polyglycerol, for example Isolan™ G134 and Plurol™ Diisostearic; ethoxylated castor oil and hydrogenated ethoxylated castor oil, Simulsol™ 989; compositions comprising glyceryl stearate and stearic acid ethoxylated with between 5 mol and 150 mol of ethylene oxide, for example the composition comprising stearic acid ethoxylated with 135 mol of ethylene oxide and glyceryl stearate, sold under the name Simulsol™ 165; polyglycol or polyglyceryl polyhydroxystearates, for example Hypermer™ B246 or Arlacel™ P135, Dehymuls™ PGPH, Decaglyn™ SHS; polyethylene glycol-alkyl glycol copolymers, for instance PEG-45 dodecyl glycol copolymer such as Elfacos™ ST 9; ethoxylated sorbitan esters, for example Montanox™; mannitan esters; ethoxylated mannitan esters; sucrose esters; methylglucoside esters.

As examples of emulsifying anionic surfactants optionally present in said compositions (C) and (C') as defined previously, mention may be made of decyl phosphate, cetyl phosphate sold under the name Amphisol™, glyceryl stearate citrate; cetearyl sulfate; the arachidyl/behenyl phosphates and arachidyl/behenyl alcohols composition sold under the name Sensanov™ WR; soaps, for instance sodium stearate or triethanolammonium stearate, salified N-acylamino acid derivatives, for instance stearoyl glutamate.

As examples of emulsifying cationic surfactants optionally present in said compositions (C) and (C') as defined previously, mention may be made of amine oxides, Quaternium™ 82 and the surfactants described in the international patent application published under the number WO 96/00719 and mainly those whose fatty chain comprises at least 16 carbon atoms.

As examples of opacifiers and/or nacreous agents optionally present in said compositions (C) and (C') as defined previously, mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate and fatty alcohols including from 12 to 22 carbon atoms.

As examples of texture agents optionally present in said compositions (C) and (C') as defined previously, mention may be made of N-acylamino acid derivatives, for example lauroyl lysine sold under the name Aminohope™ LL, octenyl starch succinate sold under the name Dryflo™, myristyl polyglucoside sold under the name Montanov™ 14, cellulose fibers, cotton fibers, chitosan fibers, talc, sericite and mica.

As examples of solvents and cosolvents optionally present in said compositions (C) and (C') as defined previously, mention may be made of water, ethylene glycol, propylene glycol, butylene glycol, hexylene glycol, diethylene glycol, water-soluble alcohols such as ethanol, isopropanol or butanol, and mixtures of water and of said solvents.

As examples of oils optionally present in said compositions (C) and (C') as defined previously, mention may be made of mineral oils such as liquid paraffin, liquid petroleum jelly, isoparaffins or white mineral oils; oils of animal origin such as squalene or squalane; plant oils, such as phytosqualane, sweet almond oil, coconut kernel oil, castor oil, jojoba oil, olive oil, rapeseed oil, groundnut oil, sunflower oil, wheat germ oil, corn germ oil, soybean oil, cotton oil, alfalfa oil, poppy oil, pumpkin oil, evening primrose oil, millet oil, barley oil, rye oil, safflower oil, candlenut oil, passionflower oil, hazelnut oil, palm oil, shea butter, apricot kernel oil, beauty-leaf oil, sisymbrium oil, avocado oil, calendula oil, oils derived from flowers or vegetables; ethoxylated plant oils; synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, fatty acid monoglycerides, diglycerides and triglycerides, for instance glyceryl triheptanoate, alkylbenzoates, hydrogenated oils, poly($\alpha$-olefins), polyolefins such as poly(isobutane), synthetic isoalkanes, for instance isohexadecane, isododecane, perfluorinated oils; silicone oils, for instance dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups. In the present patent application, the term "oils" refers to compounds and/or mixtures of compounds which are water-insoluble, and which have a liquid appearance at a temperature of 25° C.

As examples of waxes optionally present in said compositions (C) and (C') as defined previously, mention may be made of beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax; silicone waxes; plant waxes; fatty alcohols and fatty acids that are solid at room temperature; glycerides that are solid at room temperature. In the present patent application, the term "waxes" refers to compounds and/or mixtures of compounds which are water-insoluble, and which have a solid appearance at a temperature of greater than or equal to 45° C.

As examples of fatty substances optionally present in said compositions (C) and (C') as defined previously, mention may be made of saturated or unsaturated, linear or branched fatty alcohols including from 8 to 36 carbon atoms, or saturated or unsaturated, linear or branched fatty acids including from 8 to 36 carbon atoms.

As examples of thickeners or gelling agents optionally present in said compositions (C) and (C') as defined previously, mention may be made of linear or branched or crosslinked polymers of polyelectrolyte type, such as the partially or totally salified acrylic acid homopolymer, the partially or totally salified methacrylic acid homopolymer, the partially or totally salified 2-methyl-[(1-oxo-2-propenyl)amino]-1-propanesulfonic acid (AMPS) homopolymer, copolymers of acrylic acid and of AMPS, copolymers of acrylamide and of AMPS, copolymers of vinylpyrrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethylacrylamide, copolymers of AMPS and of tris (hydroxymethyl)acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethylacrylamide, terpolymers of acrylic or methacrylic acid, of AMPS and of acrylamide, copolymers of acrylic acid or methacrylic acid and of alkyl acrylates, the carbon chain of which comprises between 4 and 30 carbon atoms and more particularly between 10 and 30 carbon atoms, copolymers of AMPS and of alkyl acrylates, the carbon chain of which comprises between 4 and 30 carbon atoms and more particularly between 10 and 30 carbon atoms, linear, branched or cross-linked terpolymers of at least one monomer having a free, partially salified or totally salified strong acid function, with at least one neutral monomer, and at least one monomer of formula (V):

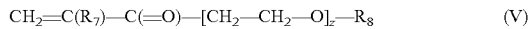

$$CH_2=C(R_7)-C(=O)-[CH_2-CH_2-O]_z-R_8 \quad (V)$$

in which $R_7$ represents a hydrogen atom or a methyl radical, $R_8$ represents a linear or branched alkyl radical including from 8 to 30 carbon atoms and z represents a number greater than or equal to 1 and less than or equal to 50.

The linear or branched or crosslinked polymers of polyelectrolyte type optionally present in said compositions (C) and (C') as defined previously may be in the form of a solution, an aqueous suspension, a water-in-oil emulsion, an oil-in-water emulsion or a powder. The linear or branched or crosslinked polymers of polyelectrolyte type optionally present in said compositions (C) and (C') as defined previously may be chosen from the products sold under the names Simulgel™ EG, Simulgel™ EPG, Sepigel™ 305, Simulgel™ 600, Simulgel™ NS, Simulgel™ INS 100, Simulgel™ FL, Simulgel™ A, Simulgel™ SMS 88, Sepinov™ EMT 10, Sepiplus™ 400, Sepiplus™ 265, Sepiplus™ S, Sepimax™ Zen, Aristoflex™ AVC, Aristoflex™ AVS, Novemer™ EC-1, Novemer™ EC 2, Aristoflex™ HMB, Cosmedia™ SP, Flocare™ ET 25, Flocare™ ET 75, Flocare™ ET 26, Flocare™ ET 30, Flocare™ ET 58, Flocare™ PSD 30, Viscolam™ AT 64 and Viscolam™ AT 100.

As examples of thickeners and/or gelling agents optionally present in said compositions (C) and (C') as defined previously, mention may be made of polysaccharides consisting only of monosaccharides, such as glucans or glucose homopolymers, glucomannoglucans, xyloglycans, galactomannans of which the degree of substitution (DS) of the D-galactose units on the main D-mannose chain is between 0 and 1, and more particularly between 1 and 0.25, such as galactomannans originating from cassia gum (DS=1/5), locust bean gum (DS=1/4), tara gum (DS=1/3), guar gum (DS=1/2) or fenugreek gum (DS=1).

As examples of thickeners and/or gelling agents optionally present in said compositions (C) and (C') as defined previously, mention may be made of polysaccharides consisting of monosaccharide derivatives, such as sulfated galactans and more particularly carrageenans and agar, uronans and more particularly algins, alginates and pectins, heteropolymers of monosaccharides and uronic acids, and more particularly xanthan gum, gellan gum, gum arabic exudates and karaya gum exudates, glucosaminoglycans.

As examples of thickeners and/or gelling agents optionally present in said compositions (C) and (C') as defined previously, mention may be made of cellulose, cellulose derivatives such as methylcellulose, ethylcellulose, hydroxypropylcellulose, silicates, starch, hydrophilic starch derivatives and polyurethanes.

As examples of stabilizers optionally present in said compositions (C) and (C') as defined previously, mention may be made of monocrystalline waxes, and more particularly ozokerite, mineral salts such as sodium chloride or magnesium chloride, silicone polymers such as polysiloxane polyalkyl polyether copolymers.

As examples of spring or mineral waters optionally present in said compositions (C) and (C') as defined previously, mention may be made of spring or mineral waters having a mineralization of at least 300 mg/l, in particular Avene water, Vittel water, Vichy basin waters, Uriage water, La Roche Posay water, La Bourboule water, Enghien-les-bains water, Saint-Gervais-les-bains water, Néris-les-bains water, Allevard-les-bains water, Digne water, Maizieres water, Neyrac-les-bains water, Lons le Saunier water, Rochefort water, Saint Christau water, Fumades water and Tercis-les-bains water.

As examples of hydrotropic agents optionally present in said compositions (C) and (C') as defined previously, mention may be made of xylene sulfonates, cumene sulfonates, hexyl polyglucoside, (2-ethylhexyl) polyglucoside and n-heptyl polyglucoside.

As examples of deodorants optionally present in said compositions (C) and (C') as defined previously, mention may be made of alkali metal silicates, zinc salts such as zinc sulfate, zinc gluconate, zinc chloride or zinc lactate; quaternary ammonium salts such as cetyltrimethylammonium salts or cetylpyridinium salts; glycerol derivatives such as glyceryl caprate, glyceryl caprylate and polyglyceryl caprate; 1,2-decanediol; 1,3-propanediol; salicylic acid; sodium bicarbonate; cyclodextrins; metallic zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, complexes of aluminum chlorohydrate and of glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, or the complex of aluminum sesquichlorohydrate and of polyethylene glycol.

As examples of sunscreens optionally present in said compositions (C) and (C') as defined previously, mention may be made of all those listed in the modified cosmetics directive 76/768/EEC, annex VII.

Among the organic sunscreens optionally present in said compositions (C) and (C') as defined previously, mention may be made of the family of benzoic acid derivatives, for instance para-aminobenzoic acids (PABA), notably monoglyceryl esters of PABA, ethyl esters of N,N-propoxy PABA, ethyl esters of N,N-diethoxy PABA, ethyl esters of N,N-dimethyl PABA, methyl esters of N,N-dimethyl PABA and butyl esters of N,N-dimethyl PABA; the family of anthranilic acid derivatives, for instance homomenthyl-N- acetyl anthranilate; the family of salicylic acid derivatives, for instance amyl salicylate, homomenthyl salicylate, ethylhexyl salicylate, phenyl salicylate, benzyl salicylate and p-isopropanolphenyl salicylate; the family of cinnamic acid derivatives, for instance ethylhexyl cinnamate, ethyl-4-isopropyl cinnamate, methyl 2,5-diisopropyl cinnamate, p-methoxypropyl cinnamate, p-methoxyisopropyl cinnamate, p-methoxyisoamyl cinnamate, p-methoxyoctyl cinnamate (p-methoxy 2-ethylhexyl cinnamate), p-methoxy-2-ethoxyethyl cinnamate, p-methoxycyclohexyl cinnamate, ethyl-α-cyano-β-phenyl cinnamate, 2-ethylhexyl-α-cyano-β-phenyl cinnamate or glyceryl di-para-methoxymono-2-ethylhexanoyl cinnamate; the family of benzophenone derivatives, for instance 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl 4'-phenylbenzophenone-2-carboxylate, 4-hydroxy-2-n-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives, for instance 2-phenylbenzimidazole-5-sulfonic acid and salts thereof; the family of triazine derivatives, for instance hydroxyphenyltriazine, (ethylhexyloxyhydroxyphenyl)(4-methoxyphenyl) triazine, 2,4,6-trianillino(p-carbo-2'-ethylhexyl-1'-oxy)-1,3,5-triazine, 4,4-((6-(((1,1-dimethylethyl)amino)carbonyl) phenyl)amino)-1,3,5-triazine-2,4-diyldiimino)bis-(2-ethylhexyl) benzoate, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl) benzotriazole; dibenzazine; dianisoylmethane, 4-methoxy-4"-t-butylbenzoylmethane; 5-(3,3-dimethyl-2-norbornylidene)-3-pentan-2-one; the family of diphenylacrylate derivatives, for instance 2-ethylhexyl 2-cyano-3,3-diphenyl-2-propenoate, ethyl 2-cyano-3,3-diphenyl-2-propenoate; the family of polysiloxanes, for instance benzylidene siloxane malonate.

Among the mineral sunscreens, also known as "mineral sunblocks", optionally present in said compositions (C) and (C') as defined previously, mention may be made of titanium oxides, zinc oxides, cerium oxide, zirconium oxide, yellow, red or black iron oxides, and chromium oxides. These mineral sunblocks may or may not be micronized, may or may not have undergone surface treatments and may optionally be in the form of aqueous or oily predispersions.

As examples of active principles optionally present in said compositions (C) and (C') as defined previously, mention may be made of vitamins and derivatives thereof, notably esters thereof, such as retinol (vitamin A) and esters thereof (for example retinyl palmitate), ascorbic acid (vitamin C) and esters thereof, sugar derivatives of ascorbic acid (such as ascorbyl glucoside), tocopherol (vitamin E) and esters thereof (such as tocopheryl acetate), vitamin B3 or B10 (niacinamide and derivatives thereof); compounds showing lightening or depigmenting action on the skin, such as w-undecelynoyl phenylalanine sold under the name Sepiwhite™ MSH, Sepicalm™ VG, the glyceryl monoester and/or diester of w-undecelynoyl phenylalanine, w-undecelynoyl dipeptides, arbutin, kojic acid, hydroquinone; compounds showing a calmative action, such as Sepicalm™ S, allantoin and bisabolol; antiinflammatory agents; compounds showing moisturizing action, such as urea, hydroxyureas, glycerol glucoside, diglycerol glucoside, polyglyceryl glucosides; polyphenol-rich plant extracts such as grape extracts, pine extracts, wine extracts and olive extracts; compounds showing slimming or lipolytic action such as caffeine or derivatives thereof, Adiposlim™, Adipoless™, fucoxanthin; N-acyl proteins; N-acyl peptides such as Matrixyl™; N-acylamino acids; N-acyl partial protein hydrolyzates; amino acids; peptides; total protein hydrolyzates; soybean extracts, for example Raffermine™; wheat extracts, for example Tensine™ or Gliadine™; plant extracts, such as tannin-rich plant extracts, isoflavone-rich plant extracts or terpene-rich plant extracts; freshwater or marine water algal extracts; marine plant extracts; marine extracts in general such as corals; essential waxes; bacterial extracts; ceramides; phospholipids; compounds showing antimicrobial action or purifying action, such as Lipacide™ C8G, Lipacide™ UG, Sepicontrol™ A5; Octopirox™ or Sensiva™ SC50; compounds showing an energizing or stimulating property such as Physiogenyl™, panthenol and derivatives thereof such as Sepicap™ MP; antiaging active agents such as Sepilift™ DPHP, Lipacide™ PVB, Sepivinol™, Sepivital™, Manoliva™, Phyto-Age™, Timecode™; Survicode™; anti-photoaging active agents; agents for protecting the integrity of the dermo-epidermal junction; agents for increasing the synthesis of components of the extracellular matrix, such as collagen, elastins and glycosaminoglycans; active agents acting favorably on chemical cellular communication, such as cytokines, or physical cellular communication, such as integrins; active agents creating a sensation of "heating" on the skin, such as skin capillary circulation activators (such as nicotinic acid derivatives) or products that create a sensation of "freshness" on the skin (such as menthol and derivatives thereof); active agents which improve the skin capillary circulation, for example venotonic agents; draining active agents; decongestant active agents such as *Ginkgo biloba*, ivy, common horse chestnut, bamboo, Ruscus, butcher's-broom, *Centella asiatica*, fucus, rosemary or willow extracts; skin tanning or browning agents, for instance dihydroxyacetone (DHA), erythrulose, mesotartaric aldehyde, glutaraldehyde, glyceraldehyde, alloxan or ninhydrin, plant extracts, for instance extracts of red woods of the genus *Pterocarpus* and of the genus *Baphia*, for instance *Pteropcarpus santalinus, Pterocarpus osun, Pterocarpus soyauxii, Pterocarpus erinaceus, Pterocarpus indicus* or *Baphia nitida*, such as those described in European patent application EP 0 971 683; agents known for their action in facilitating and/or accelerating tanning and/or browning of human skin, and/or for their action in coloring human skin, for instance carotenoids (and more particularly beta-carotene and gamma-carotene), the product sold under the brand name Carrot oil (INCI name: *Daucus carrota, Helianthus annuus* sunflower oil) by the company Provital, which contains carotenoids, vitamin E and vitamin K; tyrosine and/or derivatives thereof, known for their effect on accelerating the tanning of human skin in combination with exposure to ultraviolet radiation, for example the product sold under the brand name SunTan Accelerator™ by the company Provital, which contains tyrosine and riboflavins (vitamin B), the tyrosine and tyrosinase complex sold under the brand name Zymo Tan Complex by the company Zymo Line, the product sold under the brand name MelanoBronze™ (INCI name: Acetyl tyrosine, monk's pepper extract (Vitex Agnus-castus)) by the company Mibelle, which contains acetyl tyrosine, the product sold under the brand name Unipertan VEG-24/242/2002 (INCI name: Butylene glycol and acetyl tyrosine and hydrolyzed vegetable protein and adenosine triphosphate) by the company Unipex, the product sold under the brand name Try-Excell™ (INCI name: Oleoyl Tyrosine and *Luffa* cylindrica (Seed Oil and Oleic acid) by the company Sederma, which contains extracts of marrow seed (or loofah oil), the product sold under the trade name Actibronze™ (INCI name: hydrolyzed wheat protein and acetyl tyrosine and copper gluconate) by the company Alban Muller, the product sold under the trade name Tyrostan™ (INCI name: potassium caproyl tyrosine) by the company Synerga, the product sold under the trade name Tyrosinol (INCI name: Sorbitan Isostearate, glyceryl oleate, caproyl Tyrosine) by Synerga, the product sold under the trade name Insta-Bronze™ (INCI name: Dihydroxyacetone and acetyl tyrosine and copper gluconate) sold by the company Alban Muller, the product sold under the brand name Tyrosilane (INCI name: Methylsilanol and acetyl tyrosine) by the company Exymol; peptides known for their effect on activating melanogenesis, for example the product sold under the brand name Bronzing SF peptide powder (INCI name: Dextran and Octapeptide-5) by the company Infinitec Activos, the product sold under the trade name Melitane (INCI name: Glycerin and Aqua and Dextran and Acetyl hexapeptide-1) comprising the acetyl hexapeptide-1 known for its alpha-MSH agonist action, the product sold under the trade name Melatimes Solutions™ (INCI name: Butylene glycol, palmitoyl tripeptide-40) by the company Lipotec, sugars and sugar derivatives, for example the product sold under the brand name Tanositol™ (INCI name: Inositol) by the company Provital, the product sold under the brand name Thalitan™ (or Phycosaccharide™ AG) by the company Codif International (INCI name: Aqua and hydrolyzed algin (*Laminaria digitata*) and magnesium sulfate and manganese sulfate) containing an oligosaccharide of marine origin (guluronic acid and mannuronic acid chelated with magnesium and manganese ions), the product sold under the trade name Melactiva™ (INCI name: Maltodextrin, *Mucuna pruriens* seed extract) by the company Alban Muller, flavonoid-rich compounds, for example the product sold under the brand name Biotanning (INCI name: Hydrolyzed citrus *Aurantium dulcis* fruit extract) by the company Silab and known to be rich in lemon flavonoids (of hesperidin type);

As examples of antioxidants optionally present in said compositions (C) and (C') as defined previously, mention may be made of EDTA and salts thereof, citric acid, tartaric acid, oxalic acid, BHA (butylhydroxyanisole), BHT (butylhydroxytoluene), tocopherol derivatives such as tocopheryl acetate, mixtures of antioxidant compounds such as Dissolvine GL 47S sold by the company AkzoNobel under the INCI name: Tetrasodium glutamate diacetate.

DESCRIPTION OF THE PREFERRED EMBODIMENTS

The examples that follow illustrate the invention without, however, limiting it.

A)—Preparation of Compositions $C_1$ According to the Invention

The general procedure for the glycosylation reaction performed for preparing the compositions according to the invention is as follows:

- loading the polyol into a reactor equipped with a mechanical stirrer and a vacuum distillation assembly,
- loading rhamnose monohydrate in powder form in the stoichiometric proportions indicated in tables 1 and 2 below,
- stirring and heating until the rhamnose has totally melted,
- placing under partial vacuum to remove the water contained in the rhamnose,
- adding the catalytic system 1.0% of $H_3PO_2$ at 50% (relative to the rhamnose),
- heating until the rhamnose has disappeared.
- If necessary, neutralizing the medium with sodium hydroxide/sodium borohydride mixture, depending on the viscosity of the reaction medium.

| Operating conditions | | |
|---|---|---|
| Initial proportion of xylitol | 1 molar eq. | 1 molar eq. |
| Initial proportion of rhamnose | 1.25 molar eq. | 3.33 molar eq. |
| Catalyst | $H_3PO_2$ | $H_3PO_2$ |
| Acylation temperature | 135° C. | 135° C. |

| Characteristic of the composition obtained (mass %) | | |
|---|---|---|
| | Composition ($C_{1A}$) | Composition ($C_{1B}$) |
| Xylityl polyrhamnoside | 74.2% | 89.2% |
| Mean degree of polymerization (*) | 1.64 | 2.06 |
| Xylitan | 2.2% | 0.2% |
| Xylitol | 22.7% | 7.6% |
| Residual rhamnose | 0.6% | 3.0% |
| Water | 0.3% | n.d. |

| Operating conditions | | |
|---|---|---|
| Initial proportion of sorbitol | 1 molar eq. | 1 molar eq. |
| Initial proportion of sorbitan | 0 | 0 |
| Initial proportion of rhamnose | 1.25 molar eq. | 3.00 molar eq. |
| Catalyst | $H_3PO_2$ | $H_3PO_2$ |
| Acylation temperature | 135° C. | 135° C. |

| Characteristic of the composition obtained (mass %) | | |
|---|---|---|
| | Composition ($C_{1C}$) | Composition ($C_{1D}$) |
| Sorbityl/sorbitan/isosorbide polyrhamnoside | 74.4% | 87.7% |

-continued

| | | |
|---|---|---|
| Mean degree of polymerization* | 1.62 | 2.01 |
| Sorbitan | 1.1% | nd |
| Isosorbide | 0% | nd |
| Sorbitol | 23.6% | 9.8% |
| Residual rhamnose | 0.7% | 2.2% |
| Water | 0.2% | 0.3% |

| Operating conditions | | |
|---|---|---|
| Initial proportion of sorbitol | 0.20 molar eq. | 0.20 molar eq. |
| Initial proportion of sorbitan | 0.60 molar eq. | 0.60 molar eq. |
| Initial proportion of isosorbide | 0.20 molar eq. | 0.20 molar eq. |
| Initial proportion of rhamnose | 1.25 molar eq. | 0.6 molar eq. |
| Catalyst | $H_3PO_2$ | $H_3PO_2$ |
| Acylation temperature | 135° C. | 105° C. |

| Characteristic of the composition obtained (mass %) | | |
|---|---|---|
| | Composition ($C_{1E}$) | Composition ($C_{1F}$) |
| Sorbityl/sorbitan/isosorbide polyrhamnoside | 73.8% | 49.7% |
| Mean degree of polymerization* | 1.64 | 1.30 |
| Sorbitan | 20.5% | 35.2% |
| Isosorbide | 2.5% | 2.8% |
| Sorbitol | 2.8% | 1.3% |
| Residual rhamnose | 0.4% | 3.7% |

*the mean degree of polymerization of the polyol rhamnosides is obtained from a gas chromatography, followed by:
i) determining the mass percentages of each oligomer,
ii) normalizing the mass proportions obtained to 100%,
iii) converting into molar percentages the normalized mass percentages obtained, and
iv) calculating the mean degree of polymerization on the basis of each molar percentage obtained, weighted by the number of rhamnose units in the oligomer under consideration.

B)—Evaluation of the Moisturizing Effect of the Compositions According to the Invention—Measurement of the Production of Hyaluronic Acid on Human Fibroblast Cultures:

Normal human fibroblasts are seeded and cultured in 96-well plates in 10% FCS (fetal calf serum) culture medium, at 37° C. in a humid atmosphere containing 5% $CO_2$. When the cells reach 80% of confluence, they are or are not (control) treated with 10 ng/ml of EGF (epidermal growth factor), the positive reference for the model, the two batches of sorbityl rhamnoside at 0.1% in medium containing 2% FCS. Each condition is performed in n=4. At the end of a 72-hour incubation, the amount of hyaluronic acid excreted into the culture supernatant is measured using a specific assay kit (Hyaluronan Duo Set Assay Development Kit—Biotechne); and the amount of protein present in the cell lawns is measured using the BC Assay kit (Interchim). The amount of hyaluronic acid assayed is then expressed relative to the amount of protein per well. Means and standard deviations are calculated per condition and the level of hyaluronic acid production is evaluated by comparing the test conditions with the control condition (untreated cells). The results are collated in the following table:

| | Amount of hyaluronic acid produced | | |
|---|---|---|---|
| | Mean (ng/μg protein) | Standard deviation (ng/μg protein) | Difference relative to the control (in %) |
| Control | 16.8 | 1.29 | 0% |
| EGF (10 ng/ml) | 32.29 | 3.74 | 95% |
| Composition ($C_{1F}$) | 21.92 | 0.93 | 32% |
| Control | 9.57 | 1.90 | — |
| EGF (10 ng/ml) | 25.28 | 2.30 | 164% |
| Composition ($C_{1E}$) | 22.91 | 1.73 | 139% |

C) Formulations

In the following formulas, the percentages are expressed by weight of the formulation.

C.1 Makeup-Removing Fluid for the Face
Formula

| | |
|---|---|
| Composition ($C_{1A}$) | 10.00% |
| Methyl paraben | 0.15% |
| Phenoxyethanol | 0.80% |
| Sepicalm ™ S | 1.00% |
| Perfume/Fragrance | 0.10% |
| Water | qs 100.00% |

Procedure: Mix the various ingredients in the water with magnetic stirring, in the order indicated, and adjust the pH to about 7.

C.2 Infant Hair and Body Shampoo
Formula

| | | |
|---|---|---|
| A | Composition ($C_{1B}$) | 15.00% |
| | Proteol ™ APL | 5.00% |

|   |                    |             |
|---|--------------------|-------------|
|   | Sepicide ™ HB      | 0.50%       |
|   | Perfume/Fragrance  | 0.10%       |
| B | Water              | 20.00%      |
|   | Capigel ™ 98       | 3.50%       |
| C | Water              | qs 100.00%  |
|   | Sepicide ™ CI      | 0.30%       |
|   | Colorant           | qs          |
|   | Sodium hydroxide   | qs pH = 7.2 |

Procedure: Mix composition ($E_4$) with the Proteol™ APL and the Sepicide™ HB (Phase A). Dilute the Capigel™ 98 in a portion of the water and add it to phase A obtained previously (Phase B). Add the rest of the water to phase B, followed by the Sepicide™ CI and the colorant. Adjust the pH of the mixture to about 7.2 with sodium hydroxide.

C.3 Makeup-Removing Wipes for the Eyes
Formula

|   |                         |            |
|---|-------------------------|------------|
| A | Composition ($C_{1C}$)  | 3.00%      |
| B | Sepicide ™ HB2          | 0.50%      |
| C | Sepicalm ™ VG           | 0.50%      |
|   | Perfume/Fragrance       | 0.05%      |
| D | Water                   | qs 100.00% |

Procedure: Mix the ingredients of phase B and those of phase C in phase A until the solution is clear. Add phase D.

C.4 Mild Foaming Gel
Formula

|   |                         |             |
|---|-------------------------|-------------|
| A | Composition ($C_{1D}$)  | 8.50%       |
|   | Proteol ™ APL           | 3.00%       |
|   | Euxyl ™ PE9010          | 1.00%       |
|   | Perfume/Fragrance       | 0.10%       |
| B | Water                   | qs 100.00%  |
|   | Lactic acid             | qs pH = 6.0 |

Procedure: Dissolve the fragrance and the preserving agent Euxyl™ PE9010 in the mixture composed of composition $E_4$ and the Proteol™ APL (phase A). Add the water and adjust the pH to about 6.0 with lactic acid.

C.5 Regular-Use Shampoo
Formula

|   |                         |             |
|---|-------------------------|-------------|
| A | Composition ($C_{1E}$)  | 12.80%      |
|   | Proteol ™ OAT           | 5.00%       |
|   | Euxyl ™ PE9010          | 1.00%       |
|   | Perfume/Fragrance       | 0.30%       |
|   | Water                   | qs 100.00%  |
| B | Montaline ™ C40         | 8.50%       |
|   | Lactic acid             | qs pH = 6.0 |

Procedure: Mix all the ingredients of phase A and, after homogenization, add the Montaline™ C40 and adjust the pH to about 6.0 with lactic acid.

C.6 Ultra-Mild Baby Shampoo
Formula

|   |                         |            |
|---|-------------------------|------------|
| A | Composition ($C_{1F}$)  | 10.00%     |
|   | Amisoft ™ CS-11         | 4.00%      |
|   | Perfume/Fragrance       | 0.10%      |
|   | Sepicide ™ HB           | 0.30%      |
|   | Sepicide ™ CI           | 0.20%      |
|   | Water                   | qs 100.00% |

|   |                         |             |
|---|-------------------------|-------------|
| B | Water                   | 20.00%      |
|   | Capigel ™ 98            | 3.50%       |
|   | Tromethamine            | qs pH = 7.2 |

Procedure: Mix all the ingredients of phase A, in the order indicated, until a clear phase A is obtained. Separately, add the Capigel™ 98 to the water and then add this phase B thus prepared to phase A and adjust the pH to 7.2 using tromethamine.

C.7 Baby Cleansing Milk
Formula

|   |                         |            |
|---|-------------------------|------------|
| A | Simulsol ™ 165          | 2.00%      |
|   | Montanov ™ 202          | 1.00%      |
|   | Lanol ™ 99              | 3.00%      |
|   | Dimethicone             | 1.00%      |
|   | Isohexadecane           | 3.00%      |
| B | Water                   | qs 100.00% |
| C | Sepiplus ™ 400          | 0.30%      |
| D | Composition ($C_{1E}$)  | 6.35%      |
| E | Sepicide ™ HB           | 0.30%      |
|   | DMDM Hydantoin          | 0.20%      |
|   | Perfume/Fragrance       | 0.10%      |

Procedure: Heat, separately, phases A and B constituted by mixing the various constituents. Add phase C to the hot fatty phase and make the emulsion by pouring in the aqueous phase; homogenize for a few minutes with vigorous stirring (by means of a rotor/stator turbomixer). Next, add phase D to the hot emulsion and cool the emulsion with moderate stirring down to room temperature. Add phase E at 40° C.

C.8 Cleansing Powder Lotion for Sensitive Skin
Formula

|   |                         |             |
|---|-------------------------|-------------|
| A | Lipacide ™ C8G          | 0.95%       |
|   | Methyl paraben          | 0.10%       |
|   | Ethyl paraben           | 0.024%      |
|   | Propyl paraben          | 0.0119%     |
|   | Butyl paraben           | 0.024%      |
|   | Isobutyl paraben        | 0.0119%     |
|   | Water                   | 20.00%      |
|   | Disodium EDTA           | 0.10%       |
|   | Triethanolamine         | 1.38%       |
| B | Composition ($C_{1D}$)  | 1.80%       |
|   | Perfume/Fragrance       | 0.10%       |
| C | Sepicalm ™ S            | 0.28%       |
|   | Water                   | qs 100.00%  |
|   | Lactic acid             | qs pH = 5.2 |
| D | Micropearl ™ M310       | 5.00%       |

Procedure: Dissolve the ingredients of phase A in the water at 80° C. Separately, dissolve the fragrance in composition ($E_4$) to prepare phase B. Add the cooled phase A to phase B, then introduce the Sepicalm™ S and the remaining water. Check the final pH and adjust to about 5.2 if necessary. Next, add the Micropearl™ M310.

C.9 Infant Shower Gel
Formula

|   |                         |         |
|---|-------------------------|---------|
| A | Water                   | 56.06%  |
|   | Sepimax ™ Zen           | 3.00%   |
|   | Sepiplus ™ S            | 0.80%   |
| B | Proteol ™ OAT           | 20.80%  |
|   | Oramix ™ NS 10          | 9.30%   |
|   | Amonyl ™ 265 BA         | 5.10%   |
| C | Composition ($C_{1C}$)  | 2.00%   |
|   | Glyceryl glucoside      | 1.00%   |

-continued

| Phenoxyethanol & ethylhexyl glycerol | 1.00% |
| Perfume/Fragrance | 0.90% |
| Colorant | 0.04% |

Procedure: Disperse the Sepimax™ ZEN in the water and stir using a magnetic stirrer equipped with a deflocculator, a counter-rotating impeller and an anchor paddle, until a perfectly smooth gel is obtained. Add the Sepiplus™ S and then stir until the mixture is homogeneous. Next, add the ingredients of phase B, homogenize and individually add the additives of phase C. Adjust the pH to 6.0-6.5.

C.10 BB Cream
Formula

| A | Easynov ™ | 2.30% |
| | Lanol ™ 99 | 1.00% |
| | Sepimat ™ H10W | 1.00% |
| | Ethylhexyl methoxycinnamate | 5.00% |
| B | Cyclomethicone | 6.00% |
| | Triethoxycaprylsilane & alumina-silane & titanium oxide | 8.00% |
| | Red iron oxide & triethoxycaprylsilane | 0.24% |
| | Yellow iron oxide & triethoxycaprylsilane | 0.66% |
| | Black iron oxide & triethoxycaprylsilane | 0.09% |
| | Perfume/Fragrance | 0.10% |
| C | Water | qs 100% |
| | Sepinov ™ EMT10 | 1.20% |
| D | Composition ($C_{1D}$) | 2.00% |
| | Sepitonic ™ M3 | 1.00% |
| | Phenoxyethanol & ethylhexyl glycerol | 1.00% |

Procedure: Prepare phase B by mixing the various ingredients and homogenize using a mixer equipped with a rotor-stator system at a spin speed of 4500 rpm, for a time of 6 minutes. Prepare phase C by adding the Sepinov™ EMT10 to the mixture of water and glycerol, and homogenize using a mixer equipped with a rotor-stator system at a spin speed of 4000 rpm for 4 minutes. Add phases A and B to phase C, and stir the resulting mixture using a mechanical stirrer equipped with an anchor paddle, at a speed of 30 rpm for 2 minutes, and then at a speed of 50 rpm for 20 minutes. Add the components of phase 5 one by one and stir at a speed of 50 rpm for 25 minutes.

C.11 High-Protection Antisun Spray with an SPF of Greater than 30
Formula

| A | Montanov ™L | 1.00% |
| | Montanov ™ 82 | 1.00% |
| | C12-15 Alkyl benzoate | 17.00% |
| | Dimethicone | 3.00% |
| | Octocrylene | 6.00% |
| | Ethylhexyl methoxycinnamate | 6.00% |
| | Bis(ethylhexyloxyphenol)methoxyphenyltriazine | 3.00% |
| | Tocopherol | 0.05% |
| B | Water | qs 100% |
| C | Simulgel ™ INS 100 | 0.50% |
| | Cyclodimethicone | 5.00% |
| D | Composition ($C_{1F}$) | 3.00% |
| | Phenoxyethanol & ethylhexyl glycerol | 1.00% |
| | Perfume/Fragrance | 0.20% |
| E | Methylenebis(benzotriazolyl) Tetramethylbutylphenol | 10.00% |
| | 25% Citric acid | qs pH = 5 |

Sepicalm™ S: Mixture of N-cocoyl amino acids, sarcosine, potassium aspartate and magnesium aspartate;
Proteol™ APL: Mixture of sodium salts of N-cocoyl amino acids, obtained by acylation of amino acids characteristic of apple juice;

Sepicide™ HB: Mixture of phenoxyethanol, methyl paraben, ethyl paraben, propyl paraben and butyl paraben, which is a preserving agent;
Capigel™ 98: Acrylate copolymer;
Sepicide™ CI: Imidazoline urea, which is a preserving agent;
Sepicide™ HB: Mixture of phenoxyethanol, methyl paraben, ethyl paraben, propyl paraben, butyl paraben and isobutyl paraben, which is a preserving agent;
Sepicalm™ VG: Mixture of N-palmitoyl proline in sodium salt form and of extract of Nymphea alba blossom;
Euxyl™ PE9010: Mixture of phenoxyethanol and ethylhexyl glycerol;
Proteol™ OAT: Mixture of N-lauryl amino acids obtained by total hydrolysis of oat protein as described in WO 94/26694;
Montaline™ C40: Chloride salt of monoethanolamine cocamidopropyl betainamide;
Amisoft™ CS-11: Sodium salt of N-cocoyl glutamate;
Simulsol™ 165: Mixture of PEG-100 stearate and glyceryl stearate;
Montanov™ 202 (arachidyl alcohol, behenyl alcohol and arachidyl glucoside), is a self-emulsifying composition such as those described in EP 0 977 626;
Lanol™ 99: Isononyl isononanoate;
Sepiplus™ 400: Self-invertible inverse latex of polyacrylates in polyisobutene and including polysorbate 20, as described in WO 2005/040230;
Lipacide™ C8G: Capryloylglycine sold by the company SEPPIC;
Micropearl™ M310: Crosslinked polymethyl methacrylate polymer in powder form, used as a texture modifier;
Sepimax™ Zen (INCI name: Polyacrylate Crosspolymer-6): Thickening polymer in the form of a powder;
Sepiplus™ S (INCI name: Hydroxyethyl Acrylate/Sodium Acryloyldimethyl Taurate Copolymer & Polyisobutene & PEG-7 Trimethylolpropane Coconut Ether): Self-invertible inverse latex;
Amonyl™ 265 BA (INCI name: cocoyl betaine): foaming amphoteric surfactant;
Sepinov™ EMT10 (INCI name: Hydroxyethyl acrylate/sodium acryloyldimethyl taurate copolymer): Thickening polymer in the form of a powder;
Easynov™ (INCI name: Octyldodecanol and Octyldodecyl Xyloside and PEG-30 Dipolyhydroxystearate): Emulsifying agent of lipophilic tendency;
Sepimat™ H10 FW (INCI name: Methyl Methacrylate Crosspolymer and Squalane): Polymer used as texture agent;
Sepitonic™ M3 (INCI name: Magnesium Aspartate and Zinc Gluconate and Copper Gluconate): Mixture used as free-radical scavenger and energizing agent for cells;
Montanov™ L (INCI name: C14-22 Alcohols and C12-20 Alkylglucoside): Emulsifying agent;
Montanov™ 82 (INCI name: Cetearyl Alcohol and Cocoglucoside): Emulsifying agent;
Simulgel™ INS100 (INCI name: Hydroxyethyl Acrylate/Sodium Acryloyldimethyl Taurate Copolymer and isohexadecane and Polysorbate 60): Polymeric thickener.

The invention claimed is:
1. A composition ($C_1$) comprising, per 100% of mass:
(1)—an amount of greater than 0% by mass and less than or equal to 25% by mass of a polyol of formula (I):

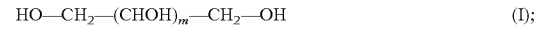

in which formula (I) m represents an integer equal to 2, 3 or 4;

(2)—an amount of greater than 0% by mass and less than or equal to 30% by mass of one or more anhydrides of said polyol of formula (I);
(3)—from 60% by mass to 95% by mass of a composition ($C_R$) represented by formula (II):

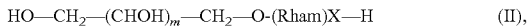

HO—CH$_2$—(CHOH)$_m$—CH$_2$—O-(Rham)X—H    (II), in which formula (II) Rham represents a rhamnose residue, m is as defined in formula (I) and x, which indicates the average degree of polymerization of said Rham residue, represents a decimal number greater than 1.0 and less than or equal to 2.5; and
(4)—an amount of greater than 0% by mass and less than or equal to 5% by mass of rhamnose.

2. The composition ($C_1$) as defined in claim 1, wherein, in formulae (I) and (II), m represents the number 2.

3. The composition ($C_1$) as defined in claim 1, wherein, in formulae (I) and (II), m represents the number 3.

4. The composition ($C_1$) as defined in claim 3, comprising, per 100% of mass:
(1)—from greater than zero up to 25% by mass of the compound of formula:

HO—CH$_2$—(CHOH)$_3$—CH$_2$—OH;

(2)—from greater than zero up to 5% by mass of the compound of formula (B$_{12}$):

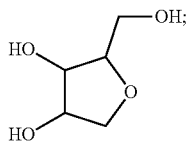

(B12)

(3)—from 70% by mass to 95% by mass of a composition ($C_{R3}$) represented by the formula HO—CH$_2$—(CHOH)$_3$—CH$_2$—O-(Rham)$_x$-H; and (4)—from greater than zero up to 2% by mass of rhamnose.

5. The composition ($C_1$) as defined in claim 1, wherein, in formulae (I) and (II), m represents the number 4.

6. The composition ($C_1$) as defined in claim 5, comprising, per 100% of mass:
(1)—from greater than zero up to 25% by mass of the compound of formula:

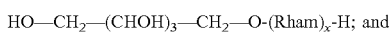

HO—CH$_2$—(CHOH)$_4$—CH$_2$—OH;

(2)—from greater than zero up to 30% by mass of the compound of formula (B$_{13}$):

(B13)

alone or in combination with the compound of formula (B$_{14}$):

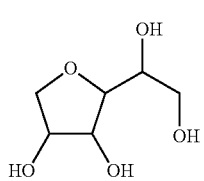

(B14)

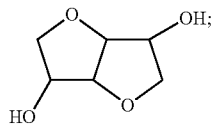

(3)—from 70% by mass to 95% by mass of a composition ($C_{R4}$) represented by the formula:

HO—CH$_2$—(CHOH)$_4$—CH$_2$—O-(Rham)X—H; and (4)—from greater than zero up to 4% by mass of rhamnose.

7. The composition ($C_1$) as defined in claim 6, comprising, per 100% of mass:
(1)—from greater than zero up to 25% by mass of the compound of formula:

HO—CH$_2$—(CHOH)$_4$—CH$_2$—OH;

(2)—from greater than zero up to 25% by mass of the compound of formula (B$_{13}$);
(2')—from greater than zero up to 5% by mass of the compound of formula (B$_{14}$);
(3)—from 70% by mass to 95% by mass of a composition ($C_{R4}$) represented by the formula:

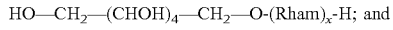

HO—CH$_2$—(CHOH)$_4$—CH$_2$—O-(Rham)$_x$-H; and (4)—from greater than zero up to 2% by mass of rhamnose.

8. A process for preparing the composition ($C_1$) as defined in claim 1, comprising:
a step a) of heating, with gentle stirring, the polyol of formula (I), until the polyol is brought to a higher temperature ($T_1$) of at least 5° C. above a melting point of the polyol to form a molten medium;
a step b) of dispersing, with stirring, rhamnose monohydrate in the previously molten medium in a desired stoichiometric ratio to form a liquid medium;
a step c) of acetalization by adding, with stirring, to the liquid medium obtained from step b), a catalytic amount of strong acid, while maintaining under partial vacuum and distilling off any water formed to form a solution; and
a step d) of neutralizing the solution obtained on conclusion of step d), to obtain said composition ($C_1$).

9. A topical cosmetic or dermocosmetic composition (C), comprising an effective amount of composition ($C_1$) as defined in claim 1.

10. A topical pharmaceutical or dermopharmaceutical composition (C'), comprising an effective amount of composition ($C_1$) as defined in claim 1.

11. A process for preparing the composition ($C_1$) as defined in claim 1, comprising:
a step a) of heating, with gentle stirring, the polyol of formula (I), until the polyol is brought to a higher temperature ($T_1$) of at least 5° C. above a melting point of the polyol to form a molten medium;
a step b) of dispersing, with stirring, rhamnose monohydrate in the previously molten medium in a desired stoichiometric ratio to form a liquid medium; and
a step c) of acetalization by adding, with stirring, to the liquid medium obtained from step b), a catalytic amount of strong acid, while maintaining under partial vacuum and distilling off any water formed to form a solution.

12. A process for preparing the composition ($C_1$) as defined in claim 2, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium;
- a step c) of acetalization by adding, with stirring, to the liquid medium obtained from step b), a catalytic amount of strong acid, while maintaining under partial vacuum and distilling off any water formed to form a solution; and
- a step d) of neutralizing the solution obtained on conclusion of step d), to obtain said composition ($C_1$).

13. A process for preparing the composition ($C_1$) as defined in claim 3, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium;
- a step c) of acetalization by adding, with stirring, to the liquid medium obtained from step b), a catalytic amount of strong acid, while maintaining under partial vacuum and distilling off any water formed to form a solution; and
- a step d) of neutralizing the solution obtained on conclusion of step d), to obtain said composition ($C_1$).

14. A process for preparing the composition ($C_1$) as defined in claim 4, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium;
- a step c) of acetalization by adding, with stirring, to the liquid medium obtained from step b), a catalytic amount of strong acid, while maintaining under partial vacuum and distilling off any water formed to form a solution; and
- a step d) of neutralizing the solution obtained on conclusion of step d), to obtain said composition ($C_1$).

15. A process for preparing the composition ($C_1$) as defined in claim 5, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium;
- a step c) of acetalization by adding, with stirring, to the liquid medium obtained from step b), a catalytic amount of strong acid, while maintaining under partial vacuum and distilling off any water formed to form a solution; and
- a step d) of neutralizing the solution obtained on conclusion of step d), to obtain said composition ($C_1$).

16. A process for preparing the composition ($C_1$) as defined in claim 6, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium;
- a step c) of acetalization by adding, with stirring, to the liquid medium obtained from step b), a catalytic amount of strong acid, while maintaining under partial vacuum and distilling off any water formed to form a solution; and
- a step d) of neutralizing the solution obtained on conclusion of step d), to obtain said composition ($C_1$).

17. A process for preparing the composition ($C_1$) as defined in claim 7, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium;
- a step c) of acetalization by adding, with stirring, to the liquid medium obtained from step b), a catalytic amount of strong acid, while maintaining under partial vacuum and distilling off any water formed to form a solution; and
- a step d) of neutralizing the solution obtained on conclusion of step d), to obtain said composition ($C_1$).

18. A process for preparing the composition ($C_1$) as defined in claim 2, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium; and
- a step c) of acetalization by adding, with stirring, to the liquid medium obtained from step b), a catalytic amount of strong acid, while maintaining under partial vacuum and distilling off any water formed to form a solution.

19. A process for preparing the composition ($C_1$) as defined in claim 3, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium; and
- a step c) of acetalization by adding, with stirring, to the liquid medium obtained from step b), a catalytic amount of strong acid, while maintaining under partial vacuum and distilling off any water formed to form a solution.

20. A process for preparing the composition ($C_1$) as defined in claim 4, comprising:
- a step a) of heating, with gentle stirring, the polyol of formula (I), until the polyol is brought to a higher temperature ($T_1$) of at least 5° C. above a melting point of the polyol to form a molten medium;
- a step b) of dispersing, with stirring, rhamnose monohydrate in the previously molten medium in a desired stoichiometric ratio to form a liquid medium; and a step c) of acetalization by adding, with stirring, to the liquid medium obtained from step b), a catalytic amount of strong acid, while maintaining under partial vacuum and distilling off any water formed to form a solution.

* * * * *